United States Patent
Gelboin et al.

(10) Patent No.: US 6,323,325 B1
(45) Date of Patent: Nov. 27, 2001

(54) AGENTS THAT BIND TO AND INHIBIT HUMAN CYTOCHROME P450 2A6

(75) Inventors: Harry V. Gelboin; Frank J. Gonzalez, both of Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/288,776

(22) Filed: Apr. 8, 1999

Related U.S. Application Data

(60) Provisional application No. 60/093,936, filed on Jul. 23, 1998.

(51) Int. Cl.$^7$ ............ G01N 33/573; G01N 33/577; C07K 16/00; C12P 21/08

(52) U.S. Cl. ............ 530/388.1; 435/4; 435/5; 435/6; 435/7; 435/7.21; 435/7.1; 435/25; 435/40.5; 435/40.51; 435/40.52; 435/696; 435/25.1; 435/968; 435/805; 436/69; 436/166; 436/169; 436/170; 436/501; 436/503; 530/387.3; 530/387.7; 530/388.15; 530/388.26; 530/387.9; 530/387.1; 530/388.85; 424/141.1

(58) Field of Search ............ 530/387.1, 387.3, 530/387.9, 388.15, 388.26, 388.85, 387.7, 388.1; 435/69.6, 4, 5, 6, 7, 7.1, 7.21, 25, 40.5, 40.51, 40.52, 252.1, 968, 805; 436/69, 166, 169, 170, 501, 503

(56) References Cited

U.S. PATENT DOCUMENTS

| | | | |
|---|---|---|---|
| 5,939,530 | 8/1999 | Gelboin et al. | 530/387.1 |

FOREIGN PATENT DOCUMENTS

| | | | |
|---|---|---|---|
| WO 92/01047 | 1/1992 | (GB) | C12N/15/00 |
| 08027195 | 1/1996 | (JP) | C07K/16/18 |
| WO 91/17271 | 11/1991 | (WO) | C12Q/1/70 |

OTHER PUBLICATIONS

Gelboin, Cytochrome P450 and Monoconal Antibodies, Pharmacological Reviews, vol. 45, No. 4, 1993, pp. 413–453.*

Yun et al., Purification and characterization of human liver microsomal cytochrome P–450 2A6, Molecular Pharmacology, vol. 40 pp. 679–685.*

Shimada et al., Cytochrome P450–dependent drug oxidation activities in liver microsomes of various animal species including rats, guinea pigs, dogs, monkeys, and humans, Archives of Toxicology, 1997, vol. 71, pp. 401–408.*

Sai et al., An inhibitory monoconal antibody to human cytochrome P450 2A6 defines its role in the metabolism of coumarin, 7–ethoxycoumarin and 4–nitroanisole in human liver., Pharmacogenetics, Apr. 1999, vol. 9, pp. 229–237.*

Tassaneeyakul et al., "Specificity of substrate and inhibitor probes for human cytochromes P450 1A1 and 1A2"., The Journal of Pharmacology and Experimental Therapeutics, vol. 265, No. 1, pp.401–407, 1993.

Pelkonen et al., "Coumarin 7–hydroxylase: characteristics and regulation in mouse and man"., Journal of Irish College of Physicians and Surgeons, vol. 22, No. 2(Suppl. 1) 1993.

Salguero et al., "A genetic polymorphism in coumarin 7–hydroxylation: Sequence of the human CYP2A genes and identification of variant CYP2A6 Alleles.", American Journal of Human Genetics, vol. 57, pp. 651–660, 1995.

Adams et al., "Specific Inhibition of Human CYP1A2 Using a Targeted Antibody.", Biochemical Pharmacology, vol. 54, pp. 189–197, 1997.

Yun et al., "Purification and Characterization of Human Liver Microsomal Cytochrome P–450 2A6"., Molecular Pharmacology, vol. 40, pp. 679–685, 11992, 1992.*

Buchert, et al., "Clinical Implications of Variable Antiarrhythmic Drug Metaloism," Pharmacogentics, 2:2–11, (1992).

Crespi, C. L. et al., "A Metabolically competent human cell line expressing five cDNAs encoding procarcinogen–activating enzymes: application to mutagenicity testing," Chem Res Toxicol, 4:566–572 (1992).

Dahl, et al., "Genetically Variable Metabolism of Antidepressants and Neuroleptic Drus in Man," Pharmacogenetics, 3:61–70 (1993).

Duescher, R. J. et al., "Human liver microsomes are efficient catalysts of 1,3–butadiene oxidation: evidence for major roles by cytochromes P450 2A6 and 2E1," Arch Biochem Biophys, 311(2):342–349 (1994).

Fernandez–Salguero, P. et al., "The CYP2A gene subfamily: species differences, regulation, catalytic activities and role in chemical carcinogenesis," Pharmacogenetics, 5:S123–128 (1995).

Fernandez–Salguero, P. et al., "A genetic polymorphism in coumarin 7–hydroxylation: sequence of the human CYP2A genes and identification of variant CYP2A6 alleles," Am J Hum Genet, 57:651–660, (1995).

Gelboin, H. V., "Cytochrome P450 and monoclonal antibodies," Pharmacol Rev, 45(4):413–453, (1993).

Gelboin, H. V. et al., "Inhibitory and noninhibitory monoclonal antibodies to human cytochrome P450 2E1," Chem Res Toxicol, 9(6):1023–1030, (1996).

(List continued on next page.)

Primary Examiner—Long V. Le
Assistant Examiner—Lisa V. Cook
(74) Attorney, Agent, or Firm—Townsend & Townsend & Crew LLP

(57) ABSTRACT

The invention provides monoclonal antibodies and other binding agents to human cytochrome P450 2A6 having advantageous properties, including capacity substantially to inhibit enzyme activity of human cytochrome P450 2A6 and lack of specific binding to other human cytochromes P450. The binding agents of the invention are useful inter alia in methods for screening drugs for metabolism by cytochrome P450 2A6, and in methods of measuring p450 2A6 levels in an individual relative to p450 2A6 levels in a control population.

6 Claims, 3 Drawing Sheets

OTHER PUBLICATIONS

Gelboin, H. V. et al., "Inhibitory and non–inhibitory monoclonal antibodies to human cytochrome P450 3A3/4," *Biochem Pharmacol*, 50(11):1841–1850, (1995).

Gelboin, H. V. et al., "A monoclonal antibody inhibitiory to human P450 2D6: a paradigm for use in combinatorial determination of individual P450 role in specific drug tissue metabolism," *Pharmacogenetics*, 7:469–477, (1997).

Goldfarb, I. et al., "Cross–reactivity of thirteen monoclonal antibodies with ten vaccinia cDNA expressed rat, mouse and human cytochrome P450s," *Biochem Pharmacol*46:787–790, (1993).

Gonzalez, F. J. et al., "Characterization of the common Genetic Defect in Humans Deficient in Debrisoquine Metabolism," *Nature*, 331(6155):442–446, (Feb. 4, 1988).

Gonzalez, F. J. et al., "Role of Human Cytochrome P–450s in Risk Assessment and Susceptibility to Environmentally Based Disease," *J. Toxicol. and Environmental Health*, 40:289–308, (1993).

Gonzalez, F. J. et al., "Expression of mammalian cytochrome P450 using vaccinia virus," *Methods Enzymol*, 206:85–92 (1991a).

Gonzalez, F. J. et al., "Expression of mammalian cytochrome P450 using Baculovirus," *Methods Enzymol*, 206:93–99, (1991b).

Guengerich, F. P. et al. "Oxidation of toxic and carcinogenic chemicals by human cytochrome P–450 enzymes," *Chem Res Toxicol*, 4(4):391–407, (1991).

Park, S. S. et al., "Monoclonal antibodies that inhibit enzyme activity of 3–methylcholanthrene–induced cytochrome P–450," *Cancer Res*, 42:1798–1808, (1982).

Park, S. S. et al., "Preparation and characterization of monoclonal antibodies to pregnenolone 16–alpha–carbonitrile inducible rat liver cytochrome P–450," *Biochem Pharmacol*, 35(17):2859–2867, (1986).

Pearce, R. et al., "Species difference and interindividual variation in liver microsomal cytochrome P450 2A enzymes: effect on coumarin, dicumarol, and tetosterone oxidation," *Arch Biochem Biophys*, 298(1):211–225, (Oct. 1992).

Pelkonen, O. et al., "Coumarin 7–hydroxylase: characteristics and regulation in mouse and man," *J. Irish Coll Phys Surg*, 22:24–28, (1993).

Rendic, S. et al., "Human cytochrome P450 enzymes: a status report summarizing their reactions, substrates, inducers, and inhibitors," *Drug Metab. Rev*, 29:413–580, (1997).

Waxman, D. J. et al., "Steroid hormone hydroxylase specificities of eleven cDNA–expressed human cytochrome P450s,"0 *Arch Biochem Biophys*, 290(1):160–166, (1991).

Yamazaki, H. et al., "7–Ethoxycoumarin O–deethylation catalyzed by cytochromes P450 1A2 and 2E1 in human liver microsomes," *Biochem Pharmacol*, 51:313–319, (1996).

Yun C. H. et al., "Purification and characterization of human liver microsomal cytochrome P–450 2A6," *Mol Pharmacol*, 40:679–685, (1991).

Pelkonen et al., "Coumarin 7–hydroxylase: characteristics and regulation in mouse and man," *J. Irish College of Physicians and Surgeons*, 22(2):24–29 (Apr. 1, 1993).

\* cited by examiner

AGENTS THAT BIND TO AND INHIBIT HUMAN CYTOCHROME P450 2A6

CROSS-REFERENCES TO RELATED APPLICATIONS

This application claims the benefit of U.S. Provisional Application No. 60/093,936 filed Jul. 23, 1998, the disclosure of which is incorporated by reference.

TECHNICAL FIELD

The present invention resides in the technical fields of immunology and enzymology.

BACKGROUND OF THE INVENTION

The cytochrome P450 family of enzymes is primarily responsible for the metabolism of xenobiotics such as drugs, carcinogens and environmental chemicals, as well as several classes of endobiotics such as steroids and prostaglandins. Members of the cytochrome P450 family are present in varying levels and their expression and activities are controlled by variables such as chemical environment, sex, developmental stage, nutrition and age.

More than 200 cytochrome P450 genes have been identified. There are multiple forms of these P450 and each of the individual forms exhibit degrees of specificity towards individual chemicals in the above classes of compounds. In some cases, a substrate, whether it be drug or carcinogen, is metabolized by more then one of the cytochromes P450.

Human CYP2A6 is an important member of the CYP superfamily and is present in liver up to 1% of the total CYP content (Yun et al., 1991). Human CYP2A6 metabolically activates the carcinogens aflatoxin B1 (Yun et al., 1991), a tobacco-specific nitrosamine 4-(methylnitrosamino)-1-(3-pyridyl)-1-butone (Crespi et al., 1991), and N-nitrosodiethylamine (Fernandez-Salguero & Gonzalez, 1995). CYP2A6 also carries out coumarin metabolism by aromatic hydroxylation in humans (Pearce et al., 1992). Coumarin 7-hydroxylation has been used as a marker for CYP2A6 activity in vitro (Yamano et al., 1990) and the basis for measuring the in vivo expression of CYP2A6 (Cholerton et al., 1992; Rautio et al., 1992). A genetic polymorphism has been found in CYP2A6 (Fernandez-Salguero et al., 1995) that is due to three variant allelic forms, i.e., CYP2A6*1, 2A6*2, 2A6*3, respectively (Daly et al., 1996).

Genetic polymorphisms of cytochromes P450 result in phenotypically-distinct subpopulations that differ in their ability to perform biotransformations of particular drugs and other chemical compounds. These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals. Eichelbaum et al., *Toxicology Letters* 64/65, 155–122 (1992). Accordingly, it is important to identify individuals who are deficient in a particular P450 enzyme, so that drugs known or suspected of being metabolized by the enzyme are not used, or used only with special precautions (e.g., reduced dosage, close monitoring) in such individuals. Identification of such individuals may indicate that such individuals be monitored for the onset of cancers.

Existing methods of identifying deficiencies in patients are not entirely satisfactory. Patient metabolic profiles are often assessed with a bioassay after a probe drug administration. Individuals with below normal cytochrome P450 activity exhibit physiologic accumulation of unmodified drug and have a high metabolic ratio of probe drug to metabolite. This bioassay has a number of limitations: lack of patient cooperation, adverse reactions to probe drugs, and inaccuracy due to coadministration of other pharmacological agents or disease effects. See, e.g., Gonzalez et al., *Clin. Pharmacokin.* 26, 59–70 (1994). Genetic assays by RFLP (restriction fragment length polymorphism), ASO PCR (allele specific oligonucleotide hybridization to PCR products or PCR using mutant/wild-type specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

A complication in patient drug choice is that most drugs have not been characterized for their metabolism by P450 2A6 and other cytochromes P450. Without knowing which cytochrome(s) p450 is/are responsible for metabolizing an individual drug, an assessment cannot be made for the adequacy of a patient's P450 profile. For such drugs, there is a risk of adverse effects if the drugs are administered to deficient metabolizers.

Monoclonal antibodies that specifically bind to 2A6 and inhibit its activity, if available, could be used to screen drugs for their metabolism by 2A6 and/or identify 2A6 deficient metabolizers by simple bioassays, thereby overcoming the problems in prior complicated methods discussed above. However, such monoclonal antibodies represent, at best, a small subset of the total repertoire of antibodies to human cytochrome P450 2A6, and have not hitherto been isolated. Although in polyclonal sera, many classes of antibody may contribute to inhibition of enzyme activity of P450 2A6 as a result of multiple antibodies in sera binding to the same molecule of enzyme, only a small percentage of these, if any, can inhibit as a monoclonal. A monoclonal antibody can inhibit only by binding in such a manner that it alone block or otherwise perturb the active site of an enzyme. The existence and representation of monoclonal antibodies with inhibitory properties thus depend on many unpredictable factors. Among them are the size of the active site in an enzyme, whether the active site is immunogenic, and whether there are any sites distal to the active site that can exert inhibition due to stearic effects of antibody binding. The only means of obtaining antibodies with inhibitory properties is to screen large numbers of hybridoma until one either isolates the desired antibody or abandons the task through failure.

Notwithstanding these difficulties, the present invention provides inter alia monoclonal antibodies that specifically bind to human cytochrome P450 2A6 and inhibit its activity.

SUMMARY OF THE INVENTION

The invention provides isolated binding agents that competes with the monoclonal antibody MAb 151-45-4 for specific binding to human cytochrome p450 2A6, and that specifically inhibit 2A6-catalyzed metabolism of coumarin by at least 50%. Preferred binding agents are monoclonal antibodies. Some binding agents lacks specific binding to at least one cytochrome P450 selected from the group consisting of human cytochromes P450 1A1, 1A2, 2B6, 2C8, 2C9, 2C19, 3A4 and 3A5. Some binding agents lack specific binding to each of human cytochromes P450 1A1, 1A2, 2B6, 2C8, 2C9, 2C19, 3A4 and 3A5. Preferred binding agents are able to specifically inhibits the enzyme activity of human cytochrome p450 2A6 by at least 80%. Some binding agents are binding fragments, such as Fab fragments.

MAb 151-45-4 is an exemplified monoclonal antibody. Some other monoclonal antibodies are analogs of MAb 151-45-4 and comprises a light chain variable domain having at least 80% sequence identity with the light chain variable domain of MAb 151-45-4 wherein the percentage sequence identity is determined by aligning amino acids in the light chain variable domains by the Kabat numbering convention, and a heavy chain variable domain having at least 80% sequence identity with the heavy chain variable domain of MAb 151-45-4 wherein the percentage sequence identity is determined by aligning amino acids in the heavy chain variable domains by the Kabat numbering convention.

The invention further provides cell lines producing monoclonal antibodies as described above. Cells lines can be eucaryotic or procaryotic.

The invention further provides methods of determining whether cytochrome P450 2A6 metabolizes a compound. Such methods entail contacting the compound with cytochrome P450 2A6 in the presence of varying amounts of the binding agent of claim 1. Metabolism of the compound is then assayed as a function of amount of binding agent, a decrease of metabolism with amount of binding agent indicating that cytochrome P450 2A6 metabolizes the compound. In some such methods, the compound is contacted with cytochrome P450 2A6 in a sample containing a collection of cytochrome P450 enzymes including 2A6.

In some methods, the sample is a tissue sample. In some methods, the collection of enzymes are obtained from a cell culture expressing the enzymes. In some methods, the compound is a drug, steroid or carcinogen. The invention further provides methods of detecting cytochrome p450 2A6. Such methods entail contacting a sample suspected of containing cytochrome P450 2A6 with a binding agent described above. One then determines whether the agent specifically binds to the sample, specific binding indicating the presence of cytochrome P450 2A6 in the sample.

The invention further provides methods of measuring p450 2A6 levels in an individual relative to p450 2A6 levels in a control population. Such methods entail contacting a sample suspected of containing cytochrome P450 2A6 from the individual and a substrate of 2A6. One then determines the p450 2A6 levels in the individual relative to p450 2A6 levels in the control population.

DEFINITIONS

Figure 1:
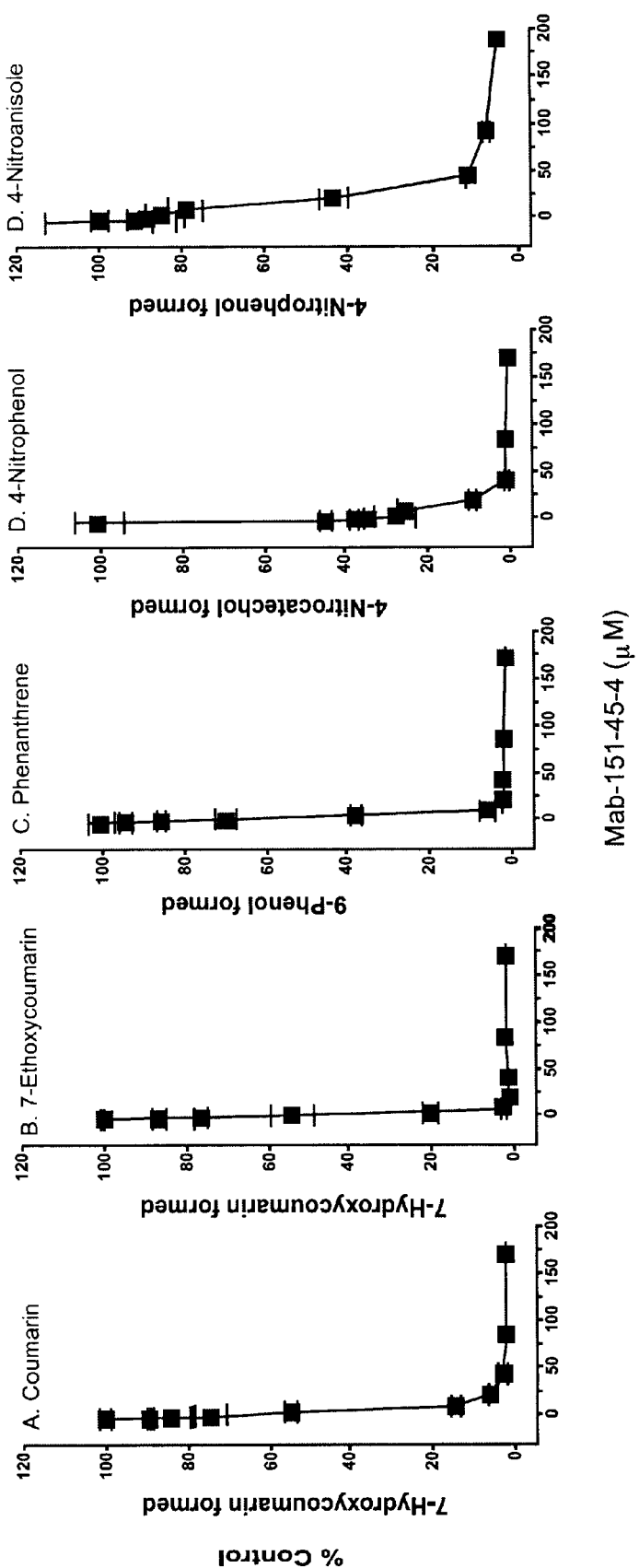
FIG. 1 shows MAb 151-45-4 inhibition of coumarin (A), 7-ethoxycoumarin (B), phenanthrene (C), 4-nitrophenol (D) and 4-nitroanisole (E) metabolism catalyzed by expressed human CYP2A6. Experiments were carried out as described in Material and Methods.

Specific binding between an antibody or other binding agent and an antigen means a binding affinity of at least $10^6$ $M^{-1}$. Preferred binding agents bind human cytochrome P450 2A6 with affinities of at least about $10^7$ $M_{-1}$, and preferably $10^8$ $M^{-1}$ to $10^9$ $^{M-1}$ or $10^{10}$ $M^{-1}$.

The term epitope means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning. That is, percent sequence identity is the percentage of aligned amino acids or nucleotides that are the same between two immunoglobulins or their coding sequences being compared.

Amino acids from the variable regions of the mature heavy and light chains of immunoglobulins are designated Hx and Lx respectively, where x is a number designating the position of an amino acids according to the scheme of Kabat et al., *Sequences of Proteins of Immunological Interest* (National Institutes of Health, Bethesda, Md. (1987) and (1991)) Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term antibody is used to mean whole antibodies and binding fragments thereof.

An isolated species means an object species (e.g., a binding polypeptide of the invention) that is the predominant species present (i.e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods.

Description of the Specific Embodiments

The invention provides monoclonal antibodies and other binding agents in isolated form that specifically bind to human cytochrome P450 2A6, and inhibit enzymic activity of 2A6. Preferred agents lack specific binding to other human cytochromes P450. The invention further provides methods of using the antibodies and other binding agents in identifying individuals with a deficient metabolizing 2A6 phenotype, and in screening drugs for metabolism by cytochrome P450 2A6.

I. Binding Agents of the Invention
A. Specificity and Functional Properties Binding agents of the invention compete with exemplary antibodies designated MAb 151-45-4 (ATCC HB-12682) for specific binding to human cytochrome P450 2A6. Production of MAb 151-45-4 is described in the Examples. The data in the Examples show that out of the total repertoire of antibodies to human cytochrome P450 2A6, only a small proportion inhibit 2A6 enzymic activity and lack specific binding to other cytochromes P450. Binding agents that compete with MAb 151-45-4 for binding to cytochrome P450 2A6 are expected to share similar inhibitory properties because inhibition by the exemplified antibodies likely arises through binding of the exemplified antibodies to an active site of 2A6, and competing agents bind to the same or closely proximate site as MAb 151-45-4. Capacity to compete with MAb 151-45-4 thus defines a select subclass of antibodies with advantageous properties from the total repertoire of antibodies to human cytochrome P450 2A6.

MAb 151-45-4 is further characterized by binding to human 2A6 on an immunoblot indicating it binds to an epitope that is not lost on treatment with a denaturing solvent.

A hybridomas producing MAb 151-45-4 (ATCC HB-12682) has been deposited at the American Type Culture Collection, 10801 University Boulevard, Manassas, Va. 20110-2209 under the Budapest Treaty and given the Accession Number indicated on Mar. 18, 1999. The cell line will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Competition is determined by an assay in which the antibody under test inhibits specific binding of a reference antibody to an antigenic determinant on human cytochrome P450 2A6. Numerous types of competitive binding assays are known for example: (see Harlow and Lane, *Antibodies, A Laboratory Manual,* Cold Spring Harbor Press (1988)). Typically, such an assay involves the use of purified human cytochrome P450 2A6, an unlabelled test antibody and a labeled reference antibody. Competitive inhibition is measured by determining the amount of label bound to human cytochrome P450 2A6 in the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. Usually, when a competing antibody is present in excess, it will inhibit specific binding of a reference antibody to human cytochrome P450 2A6 by at least 10, 25, 50 or 75%.

Binding agents of the invention typically lack specific binding (i.e., crossreactivity) to human cytochromes P450 other than 2A6, so that the binding agents can be used to detect human cytochrome P450 2A6 in the presence of other cytochromes P450. For example, binding agents of the invention typically lack specific binding to one or more of human cytochromes 1A1, 1A2, 2B6, 2C8, 2C9, 2C19, 3A4 and 3A5 as measured by ELISA and immunoblot. Some binding agents of the invention, including MAb 151-45-4 lack specific binding to all of the above human cytochromes P450.

As noted above, binding agents of the invention are characterized by capacity to inhibit human cytochrome P450 2A6-catalyzed metabolism of a substrate known to be metabolized by the enzyme. The enzyme can be assayed with any of coumarin, 7-ethoxycoumarin, 4-nitrophenol, 4-mitroamisole or phenanthrene as the substrate (see present Examples). Assays can be performed in either a microsome systems or a reconstituted systems of purified enzymes. For example, a suitable microsome system contains 1 mg/mL protein of human liver microsomes or 1.6 mg protein/mL from human lymphoblast cell lines, together with 0.2 mM substrate in a final volume of 1.0 mL of 100 mM potassium phosphate buffer, pH 7.5, and 1 mM NADPH. An exemplary reconstituted system, in place of the microsome system, contains about 20–50 nM purified human P450 2A6, 40–100 nM cytochrome b5, 100 nM NADPH-P450 reductase, 10 µg/mL phospholipids and 0.25 mM sodium cholate. Incubations are typically carried out at 37° C. for 30 min. Percentage inhibition is defined as 1-(rate of formation metabolic product in presence of test antibody/rate of formation of metabolic product in presence of control antibody), when antibody is present in excess. (The control antibody is an antibody lacking specific binding to human cytochrome P450 2A6.) Some agents of the invention inhibit metabolic capacity of isolated pure cytochrome P450 2A6 on any or all of the above substrates by at least 25%, 50%, 75%, 85%, 90% or 95%.

B. Antibodies of the Invention
1. General Characteristics

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J Mol. Biol.* 196, 901–917 (1987); *Nature* 342, 878–883 (1989); and *J. Mol. Biol.* 186, 651–663 (1989).

2. Production

Antibodies to human cytochrome P450 2A6 can be produced by a variety of means. The production of non-human monoclonal antibodies, e.g., murine or rat, can be accomplished by, for example, immunizing the animal with a preparation containing purified human cytochrome P450 or a fragment thereof. The immunogen can be obtained from a natural source, by peptides synthesis or preferably by recombinant expression. Antibody-producing cells obtained from the immunized animals are immortalized and screened for the production of an antibody which binds to human cytochrome P450 or a fragment thereof. See Harlow & Lane, *Antibodies, A Laboratory Manual* (CSHP NY, 1988) (incorporated by reference for all purposes).

Humanized forms of mouse antibodies can be generated by linking the CDR regions of non-human antibodies to human constant regions by recombinant DNA techniques. See Queen et al., *Proc. Natl. Acad. Sci.* (USA) 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to human cytochrome P450 or a fragment thereof. Human antibodies are selected by competitive binding experiments, or otherwise, to have the same epitope specificity as a particular mouse antibody, such as MAb 151-45-4. Such antibodies are particularly likely to share the useful functional properties of the exemplified antibodies.

3. Antibody Fragments

Antibodies of the invention include intact antibodies and fragments.

Typically, these fragments compete with the intact antibody from which they were derived for specific binding to human cytochrome P450 2A6, and bind with an affinity of at least $10^6$, $10^7$, $10^8$, $10^9 M^{-1}$, or $10^{10} M^{-1}$. Antibody fragments include separate heavy chains, light chains Fab, Fab' F(ab')$_2$, F$_v$, and single chain antibodies comprises a heavy chain variable region linked to a light chain variable region via a peptide spacer. Fragments can be produced by enzymic or chemical separation of intact immunoglobulins. For example, a F(ab')$_2$ fragment can be obtained from an IgG molecule by proteolytic digestion with pepsin at pH 3.0–3.5 using standard methods such as those described in Harlow and Lane, supra. Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

4. Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as *Bacillus subtilus,* and other enterobacteriaceae, such as Salmonella, Serratia, and various Pseudomonas species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (see Winnacker, *From Genes to Clones* (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., *J. Gen. Virol.* 36:59 (1977)); baby hamster kidney cells (BHK, ATCC CCL 10); Chinese hamster ovary-cells-DHFR (CHO, Urlaub and Chasin, *Proc. Nail. Acad. Sci.* (USA) 77:4216 (1980)); mouse sertoli cells (TM4, Mather, *Biol. Reprod.* 23:243–251 (1980)); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., Annals *N.Y. Acad. Sci.* 383:44–46 (1982)); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i. e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, *Protein Purification* (Springer-Verlag, N.Y., 1982). Substantially pure immunoglobulins of at least about 90 to 95% homogeneity are preferred, and 98 to 99% or more homogeneity most preferred.

5. Screening for Sequence Analogs

Many of the antibodies described above can undergo non-critical amino-acid substitutions, additions or deletions in both the variable and constant regions without loss of binding specificity or effector functions, or intolerable reduction of binding affinity (i. e., below about $10^6$ $M^{-1}$) for human cytochrome P450 2A6. Usually, the light and heavy chain variable regions of immunoglobulins incorporating such alterations exhibit at least 80, 90 or 95% sequence identity to the corresponding regions of a reference immunoglobulin from which they were derived, such as MAb 151-45-4. Preferred antibody light and heavy chain sequence variants have the same complementarity determining regions (CDRs) as the corresponding chains from one of the above reference antibodies. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; Huse, WO 92/06204.

C. Other Binding Agents of the Invention

The invention further provides nonantibody binding agents that compete with one of the exemplified antibodies for binding to human cytochrome P450 2A6. These binding agents include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds are screened for binding to human cytochrome P450 in competition with MAb 151-45-4.

II. Human Cytochrome P450 2A6

The cDNA for human cytochrome P450 2A6 has been cloned, sequenced, and expressed. Sources of other cytochromes P450 (e.g., for use in testing for lack of crossreactivity) are described by Nebert, DNA & Cell Biol. 10, 1–14 (1991); Nelson et al., *Pharmacogenetics* 6, 1–42 (1996). Insect cells (e.g., SF9) with appropriate vectors, usually derived from baculovirus, are also suitable for expressing 2A6 and other cytochromes P450. See Luckow et al., *Bio/Technology* 6:47–55 (1988); Gonzalez et al., *Meth. Enzymol.*, 206, 93–99 (1991) (incorporated by reference for all purposes). Other expression systems include yeast (Ellis et al., supra), *E. coli* (Gillam et al., *Archives Biochem. Biophys.* 319, 540–550 (1995); vaccinia virus (Gonzalez, *Pharmacol. Res.* 40, 243 (1989), and human AHH-1 lymphoblastoid cells (Crespi et al., *Carcinogenesis* 10, 295–301 (1989)).

It has been reported that in humans, the hepatic coumarin 7-hydroxylation capacity varies dramatically among individuals (Pelkonen et al, 1985; Raunio et al., 1988; Cholerton et al., 1992). This variation is at least principally due to polymorphic variation in CYP2A6, the major human coumarin 7-hydroxylase.

Humans show a wide range of 2A6 activities. Humans with normal activity are conventionally classified as extensive (EM) metabolizers, and those with less than normal activity as deficient metabolizers (DM). Normal levels can be determined by obtaining liver samples from a population of individuals and determining a mean and standard deviation of 2A6 activity in such samples. Clinical samples falling within one standard deviation of the mean are classified as EM and samples falling below one standard deviation are classified as DM. Variations of P450 activity in a tissue can result from a variety of factors including nutritional factors, chemical inducers in the environment, age, sex and general physiological or disease condition of the subject individual. MAbs to 2A6 can define the P450 variations related to genetic, age, sex, nutritional and environmental influences on P450 metabolism. The role in the metabolism of a drug by a single or multiple P450s can be important in drug discovery for understanding P450 dependent partner drug relationships that can be toxic. The P450s can be major control elements of the metabolic rates of drug metabolism as well as their pharmacologic character. The MAbs can also identify drugs toxic due to the absence of a polymorphic P450. This information can lead to better understanding of P450 activity in drug choice, dosage and efficacy.

Several therapeutically important compounds are metabolized by CYP2A6. The list includes several procarcinogens and promutagens, including the aflatoxin B1 ((Pelkonen et al., 1993, Yun et al., 1991; Salonpaa et al., 1993), several nitrosamines (Yamazaki et al., 1992; Tiano et al., 1994), and 1,3-butadiene (Duescher & Elfarra, 1994) and some drugs and chemicals, including halothane, phenothiazines (Rendic & Di Carlo, 1997), SM-12502 (Nunoya et al., 1996), 7-ethoxycoumarin, coumarin, 6-aminochrysene and nicotine (Yun et al., 1991).

III. Methods of Use

A. Identifying Compounds Metabolized by 2A6

Binding agents of the invention that inhibit enzymic activity of human cytochrome P450 2A6 can be used to assay whether compounds are metabolized by 2A6. Compounds include xenobiotics, such as a currently used and new drugs, carcinogens, pesticides or other industrial or environmental chemicals, or any endobiotic, such as a steroid hormone. The assay can indicate not only that a compound is metabolized by 2A6 but also the contribution of 2A6 to metabolizing the compound relative to other cytochromes P450 present in microsomes or cell homogenates.

Assays are performed by contacting a compound under test with human cytochrome P450 2A6 in reaction mixtures containing varying amounts of a binding agent of the invention. For example, two separate reactions may be set up, one in which the binding agent of the invention is present, and the other, a control in which the binding agent is absent. The human cytochrome P450 is often present as a microsomal extract from human or animal cells or cell lines or an extract from cell cultures expressing a collection of recombinant P450s including 2A6. The assay is performed under conditions in which 2A6 is known to be active on known substrates, such as bufurolol (see Examples). Metabolism of the compound under test is then followed from the disappearance of the compound or appearance of a metabolic product of the compound as a function of time (e.g., nmol product/sec). See, e.g., Buters et al., *Drug Metab. Dispos.* 22:688 (1994). The metabolism of the compound is analyzed as a function of the amount of binding agent present. If the metabolism quantitatively decreases with amount of binding agent, it can be concluded that 2A6 metabolizes the compound.

The percentage inhibition of 2A6 metabolism of a test compound may reflect both the inherent efficiency of a binding agent in blocking 2A6 activity and the contribution of cytochromes P450 other than 2A6 in metabolizing the compound. The inherent blocking efficiency of a binding agent can be determined by measuring inhibition of metabolism in a reaction mixture in which only 2A6 is present, or alternatively, in a reaction mixture in which a collection of cytochromes P450 are present but the substrate is known to be metabolized only by 2A6. Comparison of the percentage inhibition determined in these circumstances with the percentage inhibition of metabolism of a test substrate when a mixture of cytochromes P450 are present indicates the relative contributions of 2A6 and other enzymes in the mixture to metabolism of the test substrate. For example, if metabolism of a control substrate is inhibited by a binding agent by 90% and metabolism of a test substrate by a mixture of cytochromes P450 including 2A6 is inhibited 45%, it can be concluded that in the mixture, 2A6 contributes about 45/90=50% of metabolizing activity on the test substrate. Binding agents having a high degree of inhibition (e.g., at least about 90%) of a known substrate are particularly effective for quantitative analysis as described above.

The anti 2A6 Mab can also be used to identify substrates metabolized by CYP2A6 in human liver tissues. Recognition of the nature and contribution of CYP2A6 in individuals can permit studies of drug-drug interactions based on competitive metabolism. MAb 151-45-4 can also be used as a reagent for CYP2A6 based metabolism studies of procarcinogens and promutagens. MAb 151-45-4 can also be used in drug metabolism studies involving drug disposition, activation and therapeutic applications.

Information made available by the above methods can be exploited in a number of applications. Drugs determined to be processed by 2A6 should in general not be prescribed to patients deficient in 2A6 metabolism, or should be prescribed in reduced amounts or with close monitoring. Particular caution is needed in combination therapies involving two drugs metabolized by the 2A6 pathways. The information can also be valuable in drug design and screening. That is drugs can be designed or screened such that they are metabolized to a significant extent by several P450 enzymes, and are not therefore likely to cause side effects in those deficient in any single enzymes. Recognition that a carcinogen or other environmental toxin is deactivated by 2A6 signals that deficient metabolizers are at particular risk from the carcinogen or compound. Conversely, recognition that a carcinogen or other environmental toxin is activated to harmful form by 2A6 indicates that deficient metabolizers are less prone to harm from exposure to such a compound relative to extensive metabolizers.

B. Use of Agents for Diagnosing Metabolic Phenotype

The binding agents are useful diagnostics to determine a patient's metabolic profile prior to treatment with a drug known or suspected to be metabolized by 2A6. Patients identified as defective in 2A6 metabolism can be given alternative therapy, a lower dosage or additional monitoring to avoid damaging side effects from their DM phenotype.

Recent reports have speculated that the genetic polymorphism of CYP2A6 may relate to some level of cancer risk (Fernandez-Salguero et al., 1995; Gullsten et al., 1997). Thus identification and quantification of the amount and catalytic activities of CYP2A6 in individuals can provide useful information on the polymorphic distribution of CYP2A6, its variation among individuals, and its possible relationship of risk to cancer and other diseases.

Diagnosis can be performed as described below.

1. Binding Assay

Binding agents of the invention are useful for the quantitative measurement of the amount of individual P450 proteins in a sample, which may contain multiple forms of other P450 proteins. Binding between binding agent and cytochrome P450 2A6 in the sample can be detected by radioimmunoassay, ELISA or immuno blotting (see Harlow and Lane, supra). The type of immunoassay can be tailored to the particular application. In radioimmunoassay, the binding agent of the invention is typically labeled. In ELISA, the binding agent is typically unlabelled and detected using a secondary labeled reagent with affinity for the binding agent (e.g., anti-IgG $^{35}$S-or $^{3}$H-labeled MAb). Immuno blots are particularly useful for screening a sample with a panel of antibodies to different cytochromes P450.

These assays can be tailored to measure p450 2A6 levels in an individual relative to p450 2A6 levels in a control population. The method entails contacting a sample suspected of containing cytochrome P450 2A6 from the individual with a 2A6 substrate. One then determines the p450 2A6 levels in the individual relative to the 2A6 levels in a control population.

C. Other Uses

The binding agents of the invention can also be used for affinity purification of cytochrome P450 2A6. The basic procedure for affinity purification requires only one or two steps and can yield highly purified milligram quantities of cytochrome P450 2A6. For example, the binding agent can be covalently bound to Sepharose™, which is made into the form of either column or a slurry for batch purification. A sample containing cytochrome P450 2A6 is them passed through the column or slurry and binds to the binding agent-linked Sepharose™. The nonbound material containing unrelated proteins and cytochromes P450 other than 2A6 are thoroughly eluted leaving the cytochrome P450 2A6, which can then be eluted and used for a variety of chemical and physical studies. See, e.g., Cheng et al., *J Biol, Chem.* 259: 12279–12284 (1948).

Monoclonal antibody based immunohistochemical methods can be applied to localize and examine the distribution cytochrome P450 2A6 after different inducer administration, during various physiological states related to nutrition, age, and sex, and in different species and tissues. Furthermore, the intracellular distribution of the cytochrome P450 2A6 can be determined in a way not possible by standard biochemical methods which generally cannot identify the presence of specific forms of cytochrome P450 proteins in isolated tissues and organelles. See, e.g., Gelboin, *Pharmacol. Rev.* 45, 413–453 (1993).

EXAMPLES

Materials and Methods

Chemicals

Coumarin, 4-nitrophenol, 4-nitroanisole, 2-nitrophenol and 7-ethoxycoumarin were purchased from Aldrich (Milwaukee, Wis.). Phenanthrene was supplied by Sigma (St. Louis, Mo.). NADPH was purchased from Boehringer Mannheim (Indianapolis, Ind.).

Media and Cells

PRMI 1640 (GIBCO) supplemented with 20% FBS (BioWittaker), 2 mM L-glutamine, and 1 mM sodium pyruvate was used as complete medium. The myeloma cell line, NS-1, supplied by the Fredrick Cancer Research and Development Center (FCRDC), and resistant to 8-azaguanine, was used as a myeloma fusion partner. After fusion, newly formed hybrids were grown in complete medium containing 100 mM hypoxanthine (H), 0.4 mM aminoperin (A), 16 mM thymidine (T) (HAT medium) supplemented with 10% HCF (IGEN, Inc.). PRMI 1640 (not supplemented) was used as the washing medium.

Preparation of Human CYP2A6 Used as an Immunogen

Human CYP2A6 cDNA was constructed into the baculovirus vector as previously described (Tamura et al., 1992). Spondoptera frugipedra (Sf9) insect cells were infected with the recombinant virus and used to express CYP2A6. 100 mL of the prepared CYP2A6 baculovirus ($5\times10^3$/mL) were added to 500 mL of Sf9 cells at a density of $1.2\times10^6$ cells/mL in a 1-liter spinner flask. The Sf9 cells containing recombinant CYP2A6 were harvested seven days postinfection by centrifugation at 1500 rpm for 10 min and homogenized in 40 mL buffer A (1 nmol CYP2A6/mL, potassium phosphate 50 mM, glycerol 20%, dithiothreitol 0.35 mM, EDTA 2 mM). The homogenate was centrifuged at 105,000 g for 60 min, the supernatant was removed and the pellet was washed with 100 mL buffer A by centrifugation at 105,000 g for 60 min. The resultant pellet was suspended in 15 buffer A with 0.8% sodium cholate, homogenized and stirred overnight at 4° C. After the homogenate was centrifuged at 105,000 g for 50 min, the supernatant containing soluble CYP2A6 was transferred to a cellulose membrane bag (Spectra/promembrane, MWCO:25,000; recorder no.: 132 552) and dialyzed in 3 liters of buffer A overnight. A baculovirus-expressed human CYP2A6 suspension (2.15 nmol/mL) was obtained and used for the immunization of mice. During the preparation and extraction, the temperature was kept at 4° C., and cytochrome P450 content was monitored by using the previously reported method (Omura & Sato, 1964).

Immunization of Mice and Production of Hybridomas

Two female Balb/c mice were immunized by i.p. injection once weekly for 3 weeks with 10 mg of baculovirus-expressed human CYP2A6 protein emulsified in 0.2 mL of complete Freund's adjuvant for the first week, and then with incomplete Freund's adjuvant thereafter (Newman et al., 1992). Three days after the third injection, one mouse was killed and the spleen removed. The fusion of myeloma cells with primed and dissociated spleen cells was carried out essentially as previously described (Park et al., 1986). Myeloma cells with spleen cells added were washed three times with washing medium by centrifugation at 500 g for 10 min. The pellet was loosened and treated with PEG 4000 (Boehringer Mannheim) with gentle shaking for 1 min period and then diluted with 35 mL of washing medium. The PEG-treated cells were centrifuged at 300 g for 10 min, and resuspended in HAT medium. The cells were counted and further diluted with HAT medium and dispensed into twenty 96-well tissue culture plates at a density of 5000 cells/well in 0.2 mL/well.

Screening for the Production of Antibodies

Indirect ELISA was used for detecting the reactivity of hybridoma supernatants or purifying antibodies and studying their binding activity. The assay was performed by the generally accepted method (Goldfarb et al., 1993) using alkaline phosphatase-conjugated goat F(ab')2 fragment to mouse IgG (H+L) from Cappel Research Products, and to mouse IgG (γ chain specific) or to mouse IgM (μ chain specific) from Jackson Immuno-Research Laboratories. Beckman immunoassay plates were coated with partially purified lysate of Sf9 cells infected with either wild type baculovirus or expressing CYP2A6 at 1~2 μmol/well in 100 l of 1 H-coating solution (KPI Laboratories). As the hybrids began to grow, the spent medium from each individual well with hybrid growth was screened for the presence of antibody to CYP2A6 as described above. Each individual well on the 96-well plates with cell growth was assigned a number. Every positive well was rescreened and then cloned using complete medium with 10% HCF. Hybrids of interest were cloned at least three times.

Isotyping and Contents of Mouse Ig

Isotyping and contents of mouse Ig was determined using the Ouchterlony immunodiffusion technique as described and provided by the mouse monoclonal antibody typing kits (The Binding Site).

Preparation of Baculovirus and Vacciniavirus Expressed CYP cDNAs coding for different CYP isozymes were constructed into vaccinia (Gonzalez et al., 1991 a) and baculovirus vectors (Gonzalez et al., 1991b). TK embryoblasts or Hep G2 cells infected with recombinant vaccinia viruses were used as expression systems for human CYP 1A2, 2B6, 2C8, 2C9, 2E1, 3A4 and 3A5. Sf9 or High-Five cells infected with recombinant baculoviruses were used as expression systems for human CYP2A6 and 2D6. The microsomes containing human lymphoblast-expressed CYP 1A1, 2A6, 2C19 were purchased from GenTest Corporation.

Preparation of Human Liver Microsomes

Human liver specimens were obtained from healthy human organ donors from the Cooperative Human Tissue Network of the Eastern Division (Philadelphia, Pa.). Liver microsomes from human were prepared as described previously (Pezzuto et al., 1978), 1978). Cytochrome P450 content (Omura & Sato, 1964) and protein concentration (Lowry et al., 1951) were determined according to procedures previously described.

Immunoblot Assay

Proteins from the Sf9, High-Five, mammalian TK-embryoblasts, HepG2 cells infected with wild type and recombinant baculovirus or vaccinia virus, respectively, were separated by electrophoresis on SDS-polyacrylamide gels, transferred onto nitrocellulose filters, and probed with MAbs from cell culture or ascites fluid (Gelboin et al., 1995). MAb binding was detected using alkaline phosphatase-conjugated goat $F(ab')_2$ anti-mouse IgG (H+L) as described above.

Preparation of MAbs in Culture Fluids and Ascites

Cloned hybrids producing desired MAbs were grown in flasks containing serum-free medium (Ultra ODMA-BioWittaker) at a concentration of $5\times10^5$/mL for 3–5 days. Cells were removed by centrifugation, and the resultant supernate was concentrated with a Filtron Macrosep Concentrator (mol. Wt. cutoff 30,000). Ascites fluid was prepared as previously described (Park et al., 1986).

MAb inhibition of CYP Catalyzed Metabolism

MAbs (1~200 pmol) were preincubated with individual expressed CYPs (10~50 pmol) or human liver microsomes (total CYPs 150 pmol) at 37° C. for 5 min. Substrate (0.1 mM) and NADPH (1 mM) were added to a final volume of 1.0 mL to initiate the reaction. The substrates used were coumarin, 7-ethoxycoumarin, phenanthrene, 4-nitrophenol and 4-nitroanisole. After 15 min further incubation, the reaction was terminated by adding 0.5 mL C13CCOOH (10%, v/v) and 9 mL dichloromethane (DCM). Hy Hel (IgG against hen egg white lysozyme) at an amount of protein equivalent to MAbs was used as control. The combinatorial method with multiple MAbs was used as previously described (Gelboin et al., 1997). Internal standards for metabolite quantitation were banzo[α]pyrene-trans-4,5-dihydrodiol for coumarin and 7-ethoxycoumarin, banzo[α]pyrene-trans-9,10-dihydrodiol (D4) for phenanthrene, and 2-nitrophenol for 4-nitrophenol and 4-nitroanisole. Extracts of the metabolic products were analyzed by reverse phase high performance liquid chromatography (HPLC) as described below.

High Performance Liquid Chromatography

HPLC was performed on a Hewlett-Packard Mode HP1050 liquid chromatography equipped with a HP model 1050 autosampler, a ternary solvent delivery system, and a multiple-wavelength detector, controlled by Hewlett-Packard HPLC2D ChemStation software installed in a Compaq DeskPro 5133 personal computer.

The metabolites of phenanthrene were analyzed as previously described (Shou et al., 1994). The analysis for the metabolites of coumarin and 7-ethoxycoumarin was performed using a reverse phase analytical column (20/20, ODS, 200H4.6 mm, TLC, Springfield, Va.) and a gradient elution of 40% methanol in 0.5% acetic acid to 100% methanol at a flow rate of 1 mL/min with monitoring at 320 nm. The retention times of 7-hydroxycoumarin, coumarin and 7-ethoxycoumarin was 8.9, 11.3 and 15.3 min, respectively. 4-Nitroanisole, 4-nitrophenol and their metabolites were separated on the reverse phase column as above, eluted with a gradient of 10% methanol in 0.05 M $KH_2PO_4$ (pH 3.0) to 60% methanol at a flow rate of 1 mL/min and monitored at 345 nm. Retention times of 4-nitroanisole, 4-nitrophenol and 4-nitrocatechol were 28.8, 20.1 and 16.0 min, respectively.

Results

Hybridoma cells were obtained by the fusion of myeloma cells with the dispersed spleen cells of mice immunized with baculovirus-expressed human CYP2A6. Of more than 500 clones examined, ELISA analysis detected sixteen hybridoma clones which were selected and produced antibodies binding to baculovirus-expressed CYP2A6. Of the 16 selected hybridoma clones, four yielded antibodies which were strongly positive with ELISA for binding to CYP2A6. These four clones, MAb 85-37-1, 104-13-8, 131-52-8 and 151-45-4 were subcloned 3 times, isotyped using the Ouchterlony immunodiffusion technique and were grown for specificity testing. The other clones were moderately or negligibly positive by the ELISA test. MAb 85-37-7 was an IgM type, and MAb 151-45-4, 131-52-8 and 104-13-8 were IgG1 types. The four selected hybridomas were tested by ELISA and immunoblotting for cross-reactivity to the other CYPs and for determining the MAb inhibitory activity for CYP2A6-catalyzed metabolism.

Monoclonal Antibody Inhibition and Cross-reactivity

All the four MAbs showed inhibitory activity to CYP2A6-catalyzed phenanthrene metabolism by greater than 93%. Table 1 shows the cross-reactivity properties of the four MAbs, 85-37-7, 104-13-8, 131-52-8 and 151-45-4 with baculovirus expressed human CYP 2C19, 2D6 and vaccinia virus-expressed CYP 1A2, 2B6, 2C8, 2C9, 2E1 and 3A4. The results of both ELISA and immunoblot analysis indicated that MAb 151-45-4 specifically bound CYP2A6 and did not react with any of the other nine baculovirus or vaccinia virus-expressed CYPs. The other three MAbs showed cross reactivity. With ELISA analysis, MAb 85-37-7 showed cross-reactivity with CYP 2C9 and 2C19, MAb 104-13-8 with CYP 2C9 and 2E1, and MAb 131-52 with CYP 3A4. With the immunoblot test, MAb 104-13-8 showed cross-reactivity with wild type protein and no binding to CYP2A6. Thus MAb 151-45-4 was the only MAb that exhibited complete specificity for CYP2A6 with no detectable cross-reactivity to the nine other human CYPs and wild type protein. MAb 151-45-4 was further developed and investigated for the specificity of its inhibitory activity to CYP2A6-catalyzed metabolism.

Inhibitory effect of MAb 151-45-4 on expressed human CYP2A6-catalyzed metabolism The MAb 151-45-4 being found highly specific for binding to CYP2A6 was further examined for its inhibition of the catalytic activity of human CYP2A6 for the metabolism of coumarin, 7-ethoxycoumarin, phenanthrene, 4-nitroanisole and 4-nitrophenol. MAb 151-45-4 inhibited the CYP2A6-catalyzed metabolism of each of these substrates by more than 94% (FIG. 1). Coumarin is a known substrate for CYP2A6 (Pearce et al., 1992) and has been used as a marker for CYP2A6-catalyzed metabolism (Patten et al., 1996). MAb 151-45-4 inhibited this CYP2A6-catalyzed conversion of coumarin to its major metabolite, 7-hydroxycoumarin by 98% (FIG. 1A). 7-Ethoxycoumarin has been reported as a substrate for CYP 1A1, 1A2, 2B6 and 2E1 (Yamazaki et al., 1996). We found that 7-ethoxycoumarin O-deethylation was also catalyzed by seven other expressed CYPs: i. e., 2A6, 2C8, 2C9, 2C19, 2D6, 3A4 or 3A5 forming the metabolite, 7-hydroxycoumarin. However, MAb 151-45-4 inhibited the 7-ethoxycoumarin metabolism catalyzed only by CYP2A6 by 94% (FIG. 1B), and did not inhibit the 7-hydroxycoumarin metabolism catalyzed by any of the other ten CYPs (Table 2). Phenanthrene is metabolized to the 9-phenol by CYP2A6. Phenanthrene is also metabolized by each of the other nine CYPs: 1A1, 1A2, 2B6, 2C8, 2C9, 2C19, 2E1, 3A4 and 3A5 to different extents (Shou et al., 1994). MAb 151-45-4 strongly inhibited the CYP2A6-catalyzed phenanthrene metabolism by 99% (FIG. 1C), and did not inhibit the phenanthrene metabolism catalyzed by any of the other nine CYPs (Table 2). 4-nitrophenol is a substrate which is also metabolized by CYP2E1 (Koop & Laethem, 1992; Tassaneeyakul et al., 1993; Mishin et al., 1996), as well as by CYP2A6 (Liu et al., 1996). CYP2A6 catalyzes the 4-nitrophenol hydroxylation to 4-nitrocatechol. The 4-nitrophenol metabolism by CYP2A6 is inhibited by 99% by MAb 151-45-4 (FIG. 1D). 4-Nitrocatechol, the metabolite of 4-nitrophenol, was also detected after incubation of 4-nitrophenol with the ten other CYPs: 1A1, 1A2, 2B6, 2C8, 2C9, 2C19, 2D6, 2E1, 3A4 and 3A5. MAb 151-45-4 showed no significant inhibition of 4-nitrophenol metabolism by any of the other ten CYPs (Table 2). 4-nitroanisole is metabolized by CYP2E1 (Gelboin et al., 1996). The 4-nitroanisole O-demethylation to 4-nitrophenol catalyzed by CYP2A6 was inhibited by 95% by MAb 151-45-4 (FIG. 1E). The MAb 151-45-4 exhibited no significant inhibition of the 4-nitroanisole metabolism by the other ten CYPs (Table 2). Thus, the MAb 151-45-4 inhibitory effect is exclusively and highly specific to CYP2A6-catalyzed metabolism.

MAb 151-45-4 Based Analysis of CYP2A6 Activities

Figure 2:
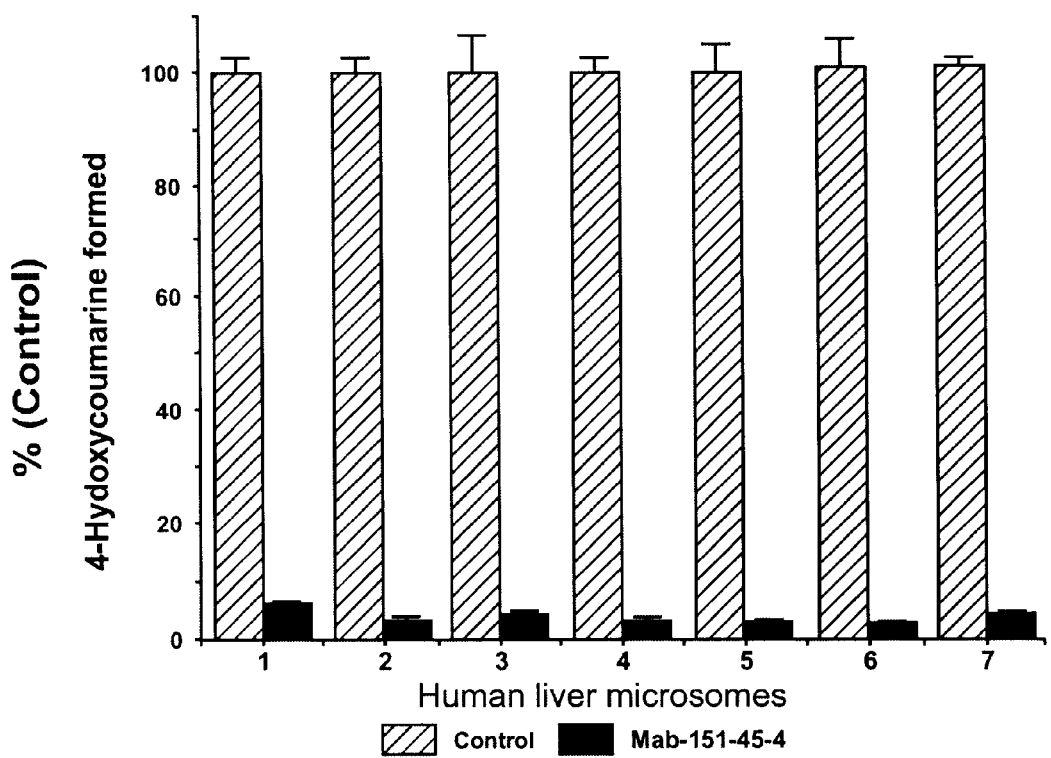
FIG. 2 shows the inhibitory effects of MAb 151-45-4 on coumarin metabolism in human liver microsomes. Experiments were carried out as described in Material and Methods.
Figure 3:
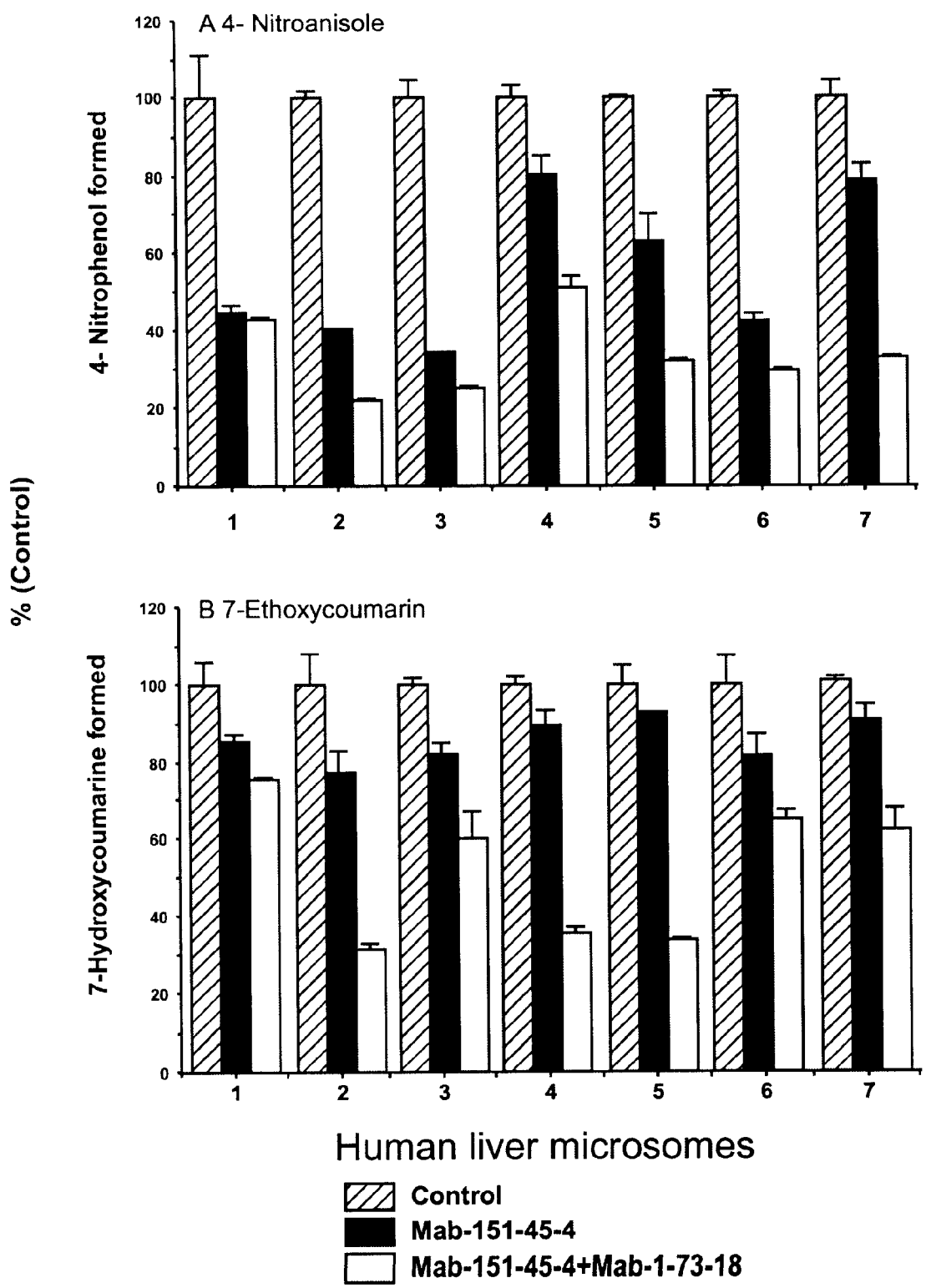
FIG. 3 shows the inhibitory effects of MAb 151-45-4 and MAb 1-73-18 on 4-nitroanisole (A) and 7-ethoxycoumarin (B) metabolism in human liver microsomes. Experiments were carried out as described in Material and Methods.

The MAb 151-45-4 was used to investigate its inhibitory effects on the metabolism of coumarin, 7-ethoxycoumarin and 4-nitroanisole in seven human liver microsome samples. FIGS. 2 and 3 showed that the metabolisms of the three substrates in human liver microsomes were inhibited to different extents by MAb 151-45-4 reflecting the role of CYP2A6 in their metabolism. In the presence of MAb 151-45-4, coumarin metabolism in all of the human liver microsome samples was inhibited by more than 94% (FIG. 2). Thus, CYP2A6 is responsible for essentially all of coumarin metabolism in human liver microsomes, which is evidence that excludes any role for other CYPs in coumarin metabolism. The inhibitory effect of MAb 151-45-4 on 4-nitroanisole metabolism in human liver microsomes ranged from 20 to 65% (FIG. 3A), which indicates that 20~65% of 4-nitroanisole conversion to 4-nitrophenol in the human liver microsomes is due to CYP2A6-catalyzed O-demethylation. The range of inhibition values reflect interindividual differences in CYP2A6-catalyzed 4-anisole metabolism. MAb 1-73-18, an anti-2E1 MAb, was previously isolated and specifically inhibits to CYP2E1 (Gelboin et al., 1996). When MAb 1-73-18 and MAb 151-45-4 were combinatorially added to measure 4-nitroanisole metabolism in human liver microsomes, the inhibition range for 4-nitroanisole metabolism was 20~65% with only MAb 151-45-4 added and 45~80% with the addition of both MAb 151-45-4 (anti 2A6) and 1-73-8 (anti2E1). The inhibition by MAb 1-73-18 of 4-nitroanisole metabolism in human liver microsomes ranged from 3 to 46% in different samples (FIG. 3A), indicating a 3~46% contribution of CYP2E1 to the total 4-nitroanisole O-demethylation in human liver microsomes. The remainder 20~55% non-inhibited 4-nitroanisole metabolism is catalyzed by CYPs other than 2A6 and 2E1.

In the case of 7-ethoxycoumarin conversion to 7-hydroxycoumarin, MAb 151-45-4 inhibits the reaction in human liver microsomes by 8~24% (FIG. 3B). The combinatorial inhibition with both a MAb 1-73-18 (anti 2E1) and MAb 151-45-1 (anti 2A6) is 25~69% for 7-ethoxycoumarin metabolism. This indicates that of the total 7-ethoxycoumarin O-deethylation in human liver microsomes, 8~24% is catalyzed by CYP2A6, 10~58% by CYP2E1 and 31~75% by CYPs other than 2E1 and 2A6. FIG. 3B shows that in general the CYP2E1 is more contributory to 7-ethoxycoumarin deethylation than is CYP2A6.

These data support the use of coumarin as a probe for CYP2A6-dependent activity (Patten et al., 1996). The entire metabolism of coumarin by the single CYP2A6 is unusual since our results with a variety of different substrates show that a large number of them were metabolized by more than one CYP, in certain cases however it seems that the metabolism of a particular substrate or the metabolism of a substrate drug through alternative metabolic pathway was determined by a single P450, in other cases by several P450s. These include phenanthrene, 4-methylanisole, 4-nitroanisole, toluene, chlorzoxazone (Gelboin et al., 1996), bufuralol (Gelboin et al., 1997), testosterone, taxol, diazepam and cyclosporin (Gelboin et al., 1995). Dextromethorphan metabolism was predominately catalyzed by CYP2D6 but a low level of activity was contributed by other CYPs (Gelboin et al., 1997). CYP2A6 also catalyzes the O-deethylation of 7-ethoxycoumarin (Raunio et al., 1988; Yamano et al., 1990; Yun et al., 1991). The total interindividual 7-ethoxycoumarin metabolism varied in different human livers, CYP2A6 was responsible for 8~24% metabolism and CYP2E1 contributed 10~50% which indicated significant inter-individual variation of CYP2A6 and 2E1 activity in human liver. 4-Nitroanisole is a substrate for CYP2E1. In this study, we observed that CYP2A6, 1A1, 1A2 and 2B1 were also good catalysts of 4-nitroanisole hydroxylation, 20~65% of 4-nitroanisole metabolism was catalyzed by human CYP2A6, and 3~46% by human CYP2E1. CYP2A6 is capable of metabolically activating many chemical carcinogens including N-nitrosodiethylamine and aflatoxin B1 (Fernandez-Salguero & Gonzalez, 1995).

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

References

Cholerton, S. et al,. Comparison of a novel thin-layer chromatographic-fluorescence detection method with a spectrofluorometric method for the determination of 7-hydroxycoumarin in human urine. *J Chromatogr* 1992 575:325–330.

Crespi, C. L. et al., A metabolically competent human cell line expressing five cDNAs encoding procarcinogen-activating enzymes: application to mutagenicity testing. *Chem Res Toxicol* 1991 4:566–572.

Daly, A. K. et al., Nomenclature for human CYP2D6 alleles. *Pharmacogenetics* 1996 6:193–201.

Duescher, R. J. et al., Human liver microsomes are efficient catalysts of 1,3-butadiene oxidation: evidence for major roles by cytochromes P450 2A6 and 2E1. *Arch Biochem Biophys* 1994 311:342–349.

Fernandez-Salguero, P. et al., The CYP2A gene subfamily: species differences, regulation, catalytic activities and role in chemical carcinogenesis. *Pharmacogenetics* 1995 5 Spec No, S123–128.

Fernandez-Salguero, P. et al., A genetic polymorphism in coumarin 7-hydroxylation: sequence of the human CYP2A genes and identification of variant CYP2A6 alleles. *Am J Hum Genet* 1995 57:651–660.

Gelboin, H. V., Cytochrome P450 and monoclonal antibodies. *Pharmacol Rev* 1993 45:413–453.

Gelboin, H. V. et al., Inhibitory and non-inhibitory monoclonal antibodies to human cytochrome P450 2E1. *Chem Res Toxicol* 1996: 9:1023–1030.

Gelboin, H. V. et al., Inhibitory and non-inhibitory monoclonal antibodies to human cytochrome P450 3A3/4. *Biochem Pharmacol* 1995 50:1841–1850.

Gelboin, H. V. et al., Inhibitiory monoclonal antibodies define the role of cytochrome P450 in human tissue: polymorphically expressed P450 2D6 as paradigm. *Pharmacogenetics* 1997: 7:467–477.

Goldfarb, I. et al., Cross-reactivity of thirteen monoclonal antibodies with ten vaccinia cDNA expressed rat, mouse and human cytochrome P450s. *Biochem Pharmacol* 1993 46:787–790.

Gonzalez, F. J. et al., Expression of mammalian cytochrome P450 using vaccinia virus. *Methods Enzymol* 1991a 206:85–92.

Gonzalez, F. J. et al., Expression of mammalian cytochrome P450 using baculovirus. *Methods Enzymol* 1991b 206:93–99.

Guengerich, F. P. et al., Oxidation of toxic and carcinogenic chemicals by human cytochrome P-450 enzymes. *Chem Res Toxicol* 1991, 4:391–407.

Gullsten, H. et al., CYP2A6 gene polymorphism and risk of liver cancer and cirrhosis. *Pharmacogenetics* 1997 7:247–250.

Kohler, G. et al., Continuous cultures of fused cells secreting antibody of predefined specificity. *Nature* 1975, 256:495–497.

Koop, D. R. et al., Inhibition of rabbit microsomal cytochrome P-450 2E1-dependent p-nitrophenol hydroxylation by substituted benzene derivatives. *Drug Metab Dispos* 1992 20:775–777.

Liu, C. et al., Baculovirus-mediated expression and characterization of rat CYP2A3 and human CYP2a6: role in metabolic activation of nasal toxicants. *Mol Pharmacol* 1996 50:781–788.

Lowry, O. H. et al., Protein measurment with the Folin reagent. *Journal Biological Chemistry* 1951 193:265–275.

Mishin, V. M. et al., The determination of cytochrome P450 2E1-dependent p-nitrophenol hydroxylation by high-performance liquid chromatography with electrochemical detection. *Anal Biochem* 1996 233:212–215.

Newman, M. A. et al., Patterns of antibody specificity during the BALB/c immune response to hen eggwhite lysozyme. *J Immunol* 1992 149(10):3260–3272.

Nunoya, K. et al., (+)-cis-3,5-dimethyl-2-(3-pyridyl) thiazolidin-4-one hydrochloride (SM-12502) as a novel substrate for cytochrome P450 2A6 in human liver microsomes. *J Pharmacol Exp Ther* 1996 277:768–774.

Omura, T. et al., The carbon monoxide-binding pigment of lover microsomes. evidence for its hemoprotein nature. *Journal Biological Chemistry* 1964 239:2370–2378.

Park, S. S. et al., Monoclonal antibodies that inhibit enzyme activity of 3-methylcholanthrene-induced cytochrome P-450. *Cancer Res* 1982 42:1798–1808.

Park, S. S. et al., Preparation and characterization of monoclonal antibodies to pregnenolone 16-alpha-carbonitrile inducible rat liver cytochrome P-450. *Biochem Pharmacol* 1986 35:2859–2867.

Patten, C. J. et al., Kinetic analysis of the activation of 4-(methylnitrosamino)-1-(3-pyridyl)-1-butanone by heterologously expressed human P450 enzymes and the effect of P450-specific chemical inhibitors on this activation in human liver microsomes. *Arch Biochem Biophys* 1996 333:127–138.

Pearce, R. et al., Species differences and interindividual variation in liver microsomal cytochrome P450 2A enzymes: effects on coumarin, dicumarol, and testosterone oxidation. *Arch Biochem Biophys* 1992 298:211–225.

Pelkonen, O. et al., Coumarin 7-hydroxylase: characteristics and regulation in mouse and man. *J Irish Coll Phys Surg* 1993 22:24–28.

Pelkonen, O. et al., Coumarin 7-hydroxylase activity in human liver microsomes. Properties of the enzyme and interspecies comparisons. *Br J Clin Pharmacol* 1985 19:59–66.

Pezzuto, J. M. et al., Metabolism of benzo(a)pyrene and (-)-trans-7,8-dihydroxy-7,8-dihydrobenzo(a)pyrene by rat liver nuclei and microsomes. *Cancer Res* 1978 38:1241–1245.

Raunio, H. et al., Immunochemical and catalytical studies on hepatic coumarin 7-hydroxylase in man, rat, and mouse. *Biochem Pharmacol* 1988 37:3889–3895.

Rautio, A. et al., Interindividual variability of coumarin 7-hydroxylation in healthy volunteers. *Pharmacogenetics* 1992 2:227–233.

Rendic, S. et al., Human cytochrome P450 enzymes: a status report summarizing their reactions, substrates, inducers, and inhibitors. *Drug Metab. Rev.* 1997 29:413–580.

Salonpaa, P. et al., Retrovirus-mediated stable expression of human CYP2A6 in mammalian cells. *Eur J Pharmacol* 1993 248:95–102.

Shou, M. et al., Regio- and stereo-selective metabolism of phenanthrene by twelve cDNA-expressed human, rodent, and rabbit cytochromes P-450. *Cancer Lett* 1994 83:305–313.

Tamura, S. et al., Baculovirus-mediated expression and functional characterization of human NADPH-P450 oxidoreductase. *Arch Biochem Biophys* 1992 293:219–223.

Tassaneeyakul, W. et al., Validation of 4-nitrophenol as an in vitro substrate probe for human liver CYP2E1 using cDNA expression and microsomal kinetic techniques. *Biochem Pharmacol* 1993 46:1975–1981.

Tiano, H. F. et al., Human CYP2A6 activation of 4-(methylnitrosamino)-1-(3-pyridyl)-1-butanone (NNK): mutational specificity in the gpt gene of AS52 cells. *Carcinogenesis* 1994 15:2859–2866.

Waxman, D. J. et al., Steroid hormone hydroxylase specificities of eleven cDNA-expressed human cytochrome P450s. *Arch Biochem Biophys* 1991 290:160–166.

Yamano, S. et al., The CYP2A3 gene product catalyzes coumarin 7-hydroxylation in human liver microsomes. *Biochemistry* 1990 29:1322–1329.

Yamazaki, H. et al., 7-Ethoxycoumarin O-deethylation catalyzed by cytochromes P450 1A2 and 2E1 in human liver microsomes. *Biochem Pharmacol* 1996 51:313–319.

Yamazaki, H. et al., Cytochrome P450 2E1 and 2A6 enzymes as major catalysts for metabolic activation of N-nitrosodialkylamines and tobacco-related nitrosamines in human liver microsomes. *Carcinogenesis* 1992 13:1789–1794.

Yun, C. H. et al., Purification and characterization of human liver microsomal cytochrome P-450 2A6. *Mol Pharmacol* 1991 40:679–685.

What is claimed is:

1. A monoclonal antibody MAb 151-45-4 (ATCC HB-12682) for specific binding to human cytochrome P450 2A6, and that specifically inhibits 2A6-catalyzed metabolism of coumarin by at least 50%.

2. The monoclonal antibody of claim 1 that lacks specific binding to at least one cytochrome P450 selected from the group consisting of human cytochromes P450 1A1, 1A2, 2B6, 2C8, 2C9, 2C19, 3A4 and 3A5.

3. The monoclonal antibody of claim 1 that lacks specific binding to each of human cytochromes P450 1A1, 1A2, 2B6, 2C8, 2C9, 2C19, 3A4 and 3A5.

4. The monoclonal antibody of claim 1 that specifically inhibits 2A6-catalyzed metabolism of coumarin by at least 80%.

5. The monoclonal antibody of claim 1 that is MAb 151-45-4 (ATCC HB-12682) or a binding fragment thereof.

6. The monoclonal antibody of claim 1 that is a mouse antibody.

* * * * *